United States Patent
Brehm et al.

(10) Patent No.: US 10,661,071 B2
(45) Date of Patent: May 26, 2020

(54) HOSE CLAMP FOR A BLOOD TREATMENT DEVICE

(71) Applicant: FRESENIUS MEDICAL CARE DEUTSCHLAND GMBH, Bad Homburg (DE)

(72) Inventors: Winfried Brehm, Hofheim (DE); Gerhard Wiesen, Bad Homburg (DE); Karsten Fischer, Schweinfurt (DE)

(73) Assignee: FRESENIUS MEDICAL CARE DEUTSCHLAND GMBH, Bad Homberg (DE)

( * ) Notice: Subject to any disclaimer, the term of this patent is extended or adjusted under 35 U.S.C. 154(b) by 35 days.

(21) Appl. No.: 15/775,949

(22) PCT Filed: Nov. 11, 2016

(86) PCT No.: PCT/EP2016/001879
§ 371 (c)(1),
(2) Date: May 14, 2018

(87) PCT Pub. No.: WO2017/080663
PCT Pub. Date: May 18, 2017

(65) Prior Publication Data
US 2018/0353746 A1    Dec. 13, 2018

(30) Foreign Application Priority Data
Nov. 13, 2015    (DE) .......................... 10 2015 014 741

(51) Int. Cl.
*A61M 39/28*    (2006.01)
*A61M 5/168*    (2006.01)
*A61M 1/36*    (2006.01)

(52) U.S. Cl.
CPC .......... *A61M 39/284* (2013.01); *A61M 1/367* (2013.01); *A61M 5/16813* (2013.01); *A61M 39/281* (2013.01)

(58) Field of Classification Search
CPC ................ A61M 39/284; A61M 1/367; A61M 5/16813; A61M 9/281
See application file for complete search history.

(56) References Cited

U.S. PATENT DOCUMENTS 4,061,142 A * 12/1977 Tuttle ...................... A61M 1/30
604/34
2010/0057016 A1 * 3/2010 Dale .................. A61M 5/16881
604/250

(Continued)

FOREIGN PATENT DOCUMENTS

CA    2913091    11/2014

*Primary Examiner* — Umashankar Venkatesan
(74) *Attorney, Agent, or Firm* — Jacobson Holman, PLLC.

(57) ABSTRACT

The invention relates to a hose clamp for a blood treatment device, wherein the hose clamp has a housing (4) and an electromagnetically driven compression piece (1), with the electromagnetic drive of the compression piece (1) being configured such that the compression piece (1) is opened against a mechanical restoring force (A) in a state of the hose clamp with an applied current and is closed by the mechanical restoring force (A) in a currentless state of the hose clamp; wherein the hose clamp has, in addition to the electromechanical drive, a mechanical actuator (5) with which the compression piece (1) can be opened manually against the mechanical restoring force (A) in the currentless state of the hose clamp; and wherein the contact elements (6, 7) of the actuator (5) and of the compression piece (1) are configured such that they form a mechanical connection between the actuator (5) and the compression piece (1) after an opening of the compression piece (1) in the currentless (Continued)

Figure 1:
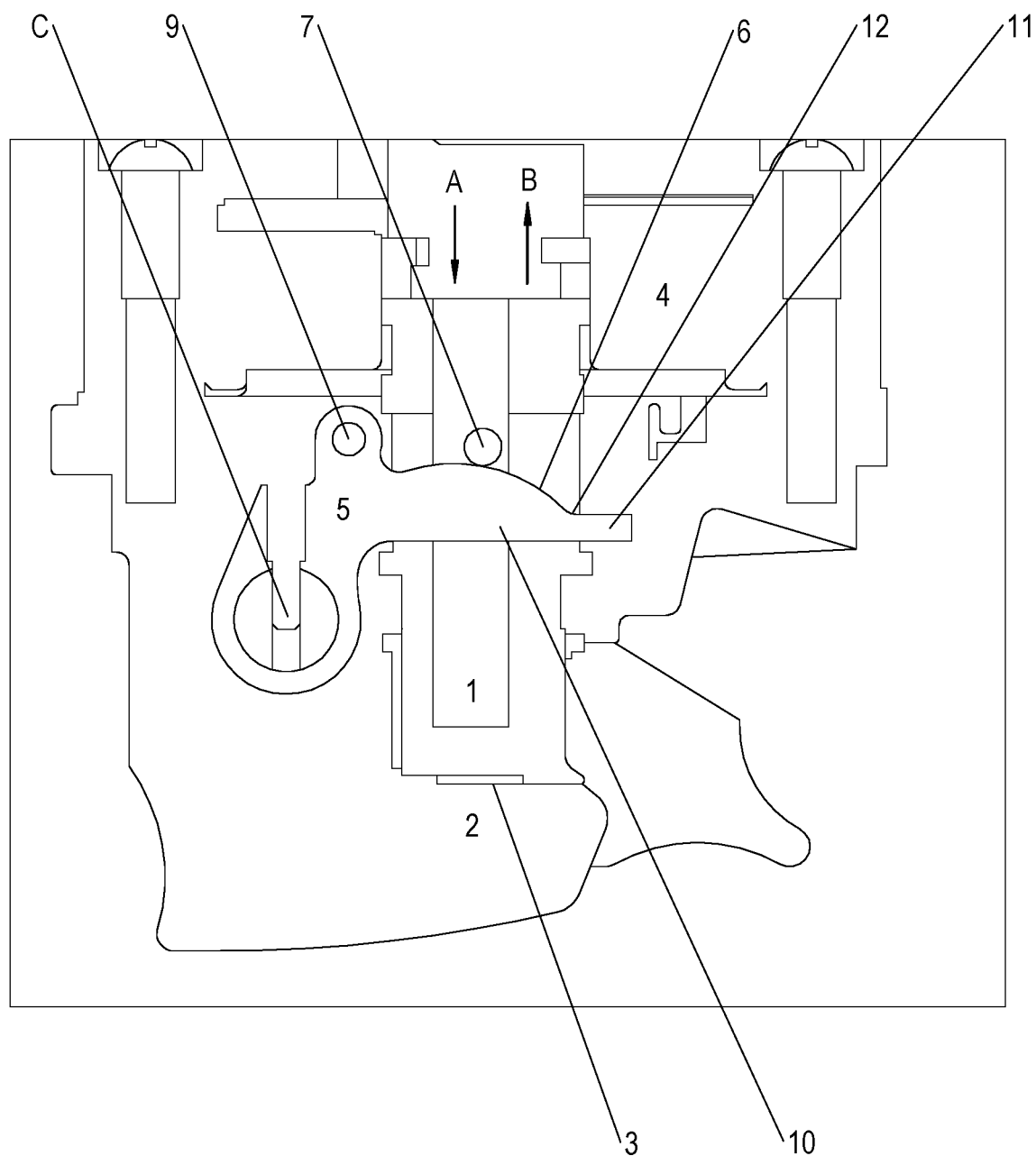

state, said connection preventing another closing of the compression piece (1) in the currentless state of the hose clamp by the mechanical restoring force (A) and being released in the state of the hose clamp with an applied current.

18 Claims, 3 Drawing Sheets

(56) References Cited

U.S. PATENT DOCUMENTS

| | | | | |
|---|---|---|---|---|
| 2013/0317454 A1* | 11/2013 | Grant | ............... | A61M 39/284 604/250 |
| 2017/0120035 A1* | 5/2017 | Butterfield | .......... | A61M 5/1409 |

* cited by examiner

HOSE CLAMP FOR A BLOOD TREATMENT DEVICE

The invention relates to a hose clamp for a blood treatment device, to a blood treatment device having such a hose clamp, and to a method for removing and/or inserting a hose kit from or into such a blood treatment device.

Blood treatment devices have a hose clamp as a safety feature that serves the clamping of a hose of the extracorporeal blood circuit. The clamp makes it possible to separate the patient from the extracorporeal blood circuit in the course of the treatment, in particular to avoid blood loss. It is known for safety reasons to configure the clamp such that it closes and thus separates the patient from the extracorporeal blood circuit in the currentless state that can be caused, for example, by a power cut.

In the conventional three-shift operation of blood treatment centers and, for example, dialysis centers, the devices are already prepared for the next day after the last treatment of the evening and the hose kit serving as the extracorporeal blood circuit is inserted.

Since the device is, however, as a rule in the currentless state overnight, the clamp as rule clamps the hose over a longer period of time. This results in a long-term crushing of the hose that is thereby irreversibly deformed in the affected region. This can result in unwanted turbulence in operation.

It is the aim of the invention to avoid this disadvantage.

Against this background, the invention relates to a hose clamp for a blood treatment device that has a housing and an electromechanically driven compression piece. The electromechanical drive of the compression piece is configured such that it is opened against a mechanical restoring force in a state of the hose clamp with an applied current and is closed by the mechanical restoring force in a currentless state of the hose clamp. In addition to the electromechanical drive, the hose clamp has a mechanical actuator with which the compression piece can be opened manually against the mechanical restoring force in the currentless state of the hose clamp. Provision is made in accordance with the invention that the contact elements of the actuator and of the compression piece are configured such that they form a mechanical connection between the actuator and the compression piece after an opening of the compression piece in the currentless state, said connection preventing another closing of the compression piece in the currentless state of the hose clamp by the mechanical restoring force and being released in the state of the hose clamp with an applied current.

In an embodiment, one contact element, preferably the contact element at the compression piece side, is a projection and the other contact element, preferably the contact element at the actuator side, is a guideway. The guideway is in this respect configured such that the projection is moved along it on an actuation of the actuator. The guideway furthermore comprises a latch contour for the projection at a saddle point at which the projection is located in an open position of the compression piece. The guideway can, for example, be an edge of the actuator or a slot guide in the actuator or in the compression piece.

In an embodiment, the actuator is a pivotable lever, with the guideway preferably being arranged at a side edge of the lever arm.

In an embodiment, the guideway is at least sectionally convex and preferably of part circle shape.

In an embodiment, a stop contour is located at the end of the guideway. The stop contour is preferably located at the remote side of the saddle point. The stop contour bounds the maximum opening of the compression piece that can be reached by the actuator. The stop contour can, for example, be a linear section of the guideway that has a different gradient than the sections disposed in front of the saddle point.

In an embodiment, the projection is a pin that is preferably normal to the closing direction of the compression piece. The pin can be rotatably supported, for example, at the compression piece or at the actuator so that it rolls off along the guideway or is fixedly supported so that it slides along the guideway.

In an embodiment, the latch contour is a recess in the guideway and/or a step on the guideway. The recess can, for example, be a circular shape molded into the guideway at the saddle point, with the radius of the circular shape being able to correspond, for example, to the radius of the pin.

In an embodiment, the hose clamp has a mechanical spring, preferably a mechanical tension spring, that is connected to the actuator and to the housing and that exerts a restoring force onto the actuator against its actuation direction on the opening of the compression piece.

Against the initially named background, the invention furthermore relates to a blood treatment device, preferably to a dialysis device, having an extracorporeal blood circuit that has a line section formed as a hose, with the line section preferably forming a part of the arterial line or of the venous line of the extracorporeal blood circuit. Provision is made in accordance with the invention that a hose clamp in accordance with the invention is arranged at the line section formed as a hose.

The dialysis device can, for example, be a device for carrying out a hemodialysis, a hemodiafiltration, and/or a hemofiltration.

The hose is preferably a hose of plastic that can, for example, have a round cross-section.

The arterial line is disposed before the treatment unit of the device, for example the dialyzer of the dialysis device, and the venous line is disposed thereafter. Depending on the position of the line section, the clamp arranged thereat is an arterial clamp or a venous clamp. The line section and the clamp are preferably disposed close to the arterial port or to the venous port at which the patient is connected to the blood circuit.

The extracorporeal blood circuit can naturally have a plurality of line sections formed as a hose and the blood treatment device can naturally have a plurality of clamps of the same or different designs that engage at one or more of these line sections. The inventive step is that at least one line section formed as a hose is present at which at least one clamp in accordance with the invention is arranged.

In an embodiment, the extracorporeal blood circuit has two line sections formed as hoses, with one of these line sections forming a part of the arterial line and the other of these line sections forming a part of the venous line of the extracorporeal blood circuit. Provision can be made in this embodiment that the blood treatment device has two hose clamps in accordance with the invention, with one of these hose clamps being arranged at one of these line sections and the other one of the hose clamps being arranged at the other one of these line sections.

Against the initially named background, the invention furthermore relates to a method for removing and/or inserting a hose kit from or into a blood treatment device in accordance with the invention. The hose kit forms at least a part of the extracorporeal blood circuit and comprises the line section at which the hose clamp in accordance with the invention is arranged. Provision is made in accordance with the invention that the compression piece is opened in the currentless state by actuation of the actuator and the hose kit is subsequently removed and/or inserted in the still currentless state of the hose clamp, while the compression piece is kept open by the mechanical connection between the actuator and the compression piece.

The removal and insertion of the hose kit together stands for the exchange of the hose kit.

The hose kit can in this manner, for example, already be replaced or inserted the evening before in a dialysis center and the dialysis machine can nevertheless remain currentless overnight without the hose kit being clamped and possibly being deformed or damaged in this process.

Figure 2:
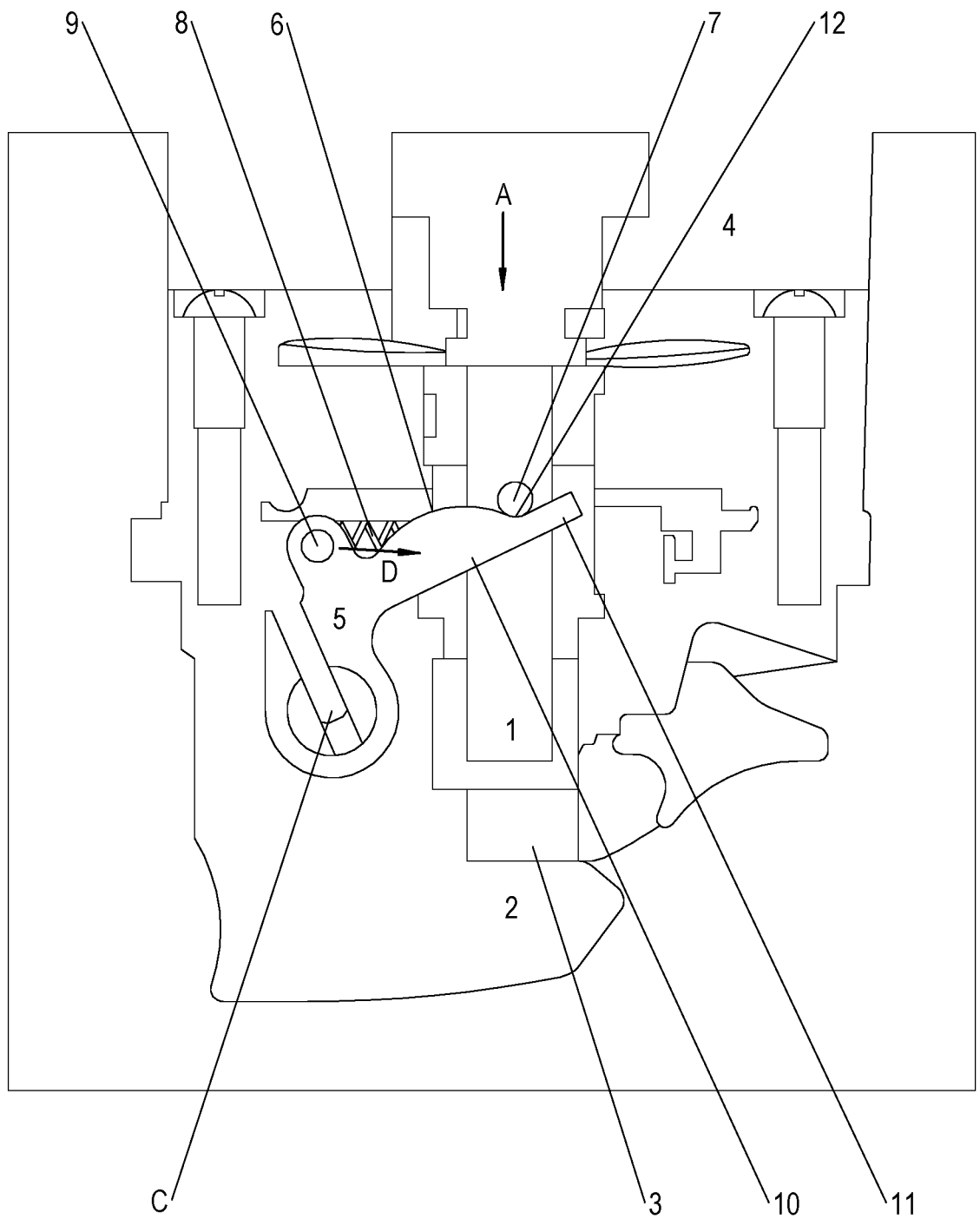
Figure 3:
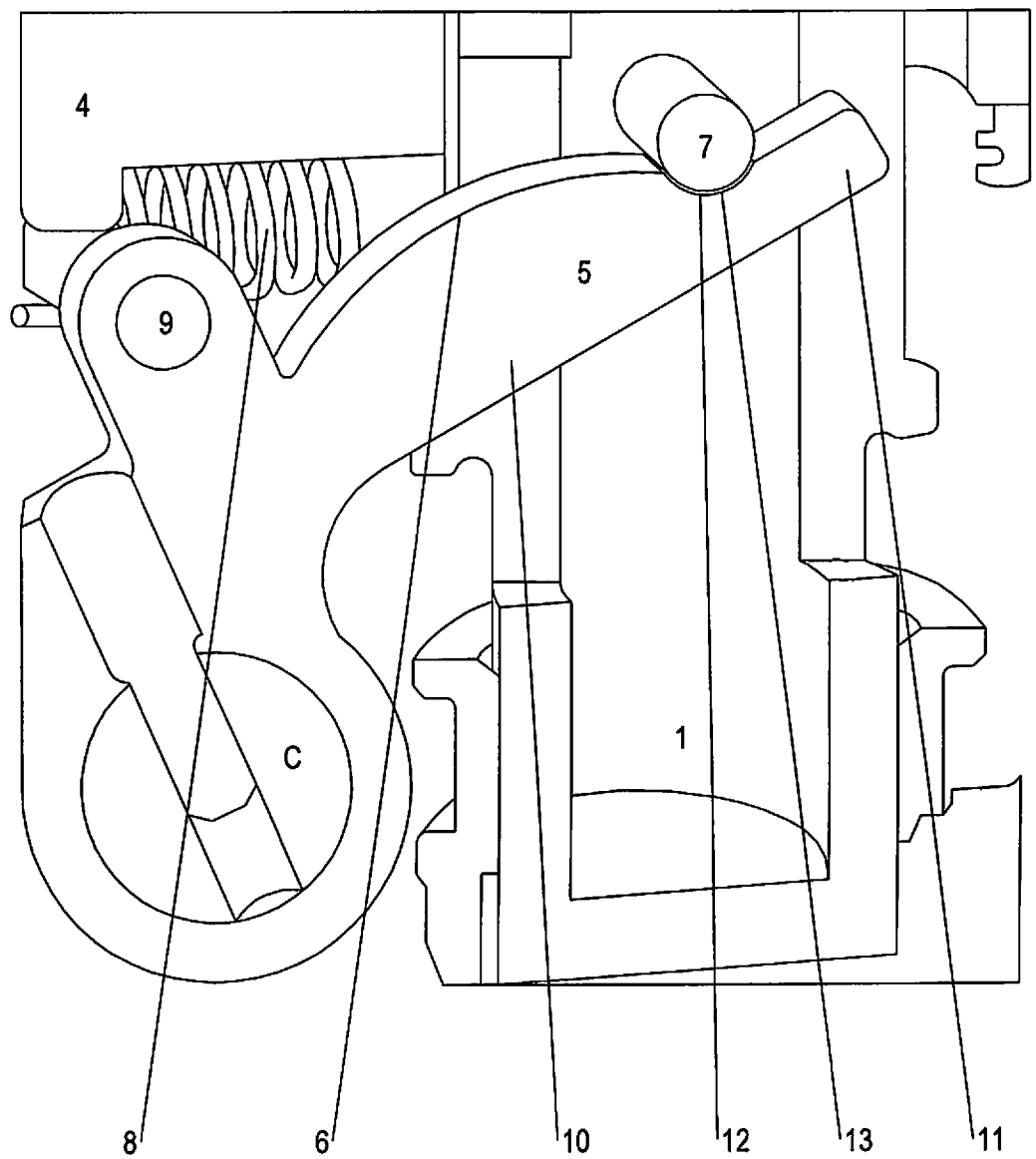

Further details and advantages of the invention result from the known systems in accordance with the invention explained in the following with reference to the Figures. There are shown in the Figures:

FIG. 1: a sectional representation of a hose clamp of the prior art in a currentless and closed state:

FIG. 2: a sectional representation of the hose clamp shown in FIG. 1 in a still currentless, but manually opened state; and FIG. 3: a sectional representation of a hose clamp in accordance with the invention in the currentless, but manually opened state.

FIGS. 1 and 2 show an already known hose clamp of a dialysis device of the prior art.

The hose clamp comprises a movable compression piece 1 and a stationary saddle 2. A cut-out 3 is formed therebetween for the reception of a plastic hose, for example of a plastic hose that forms a part section of an extracorporeal blood circuit of a dialysis machine.

The compression piece 1 is vertically displaceably supported within the clamp housing 4 (directions or positions such as "vertical", "horizontal", "up", "top", "down", "bottom", etc. relate to the representation shown and not to the actuation installation position of the hose clamp in the blood treatment device). The vertical displacement of the compression piece is controlled using an electrical mechanism not shown in any more detail in the Figures. This electrical mechanism, on the one hand, comprises a mechanical compression spring that presses the compression piece 1 downward (direction A) into the closed position shown in FIG. 1. The electrical mechanism furthermore comprises an electromagnet that draws the compression piece 1 upward (direction B) in the state with an applied current against the restoring force of the mechanical compression spring. The opening force effected by the electromagnet is larger than the closing force effected by the mechanical compression spring. The state of the clamp opened by applying current to the electromagnet is not shown in the Figures.

After the raising of the compression piece 1 by applying current to the electromagnet, a manual raising of the compression piece 1 is possible by actuating a pivotable lever 5. The lever 5 engages through an aperture of the compression piece 1 and comprises a guideway 6 that cooperates with a pin 7 that is molded or fastened to the compression piece 1. The lever 5 can be pivoted about an axis C while overcoming a mechanical counter-force out of a horizontal position of rest (FIG. 1) into a raised position (FIG. 2) by manual actuation. The mechanical counter-force is exerted in this respect, on the one hand, by the compression spring 8 that is arranged between the clamp housing 4 and a prolongation 9 of the lever 5 and, on the other hand, by the restoring force that acts on the compression piece 1 and is passed onto the lever 5 by the contact elements 6 and 7. The actuation element seated in the extension of the axis C for the manual pivoting of the lever, which can be a rotary button or a grip lever, for example, is not shown in any more detail in the Figures and is covered by the housing 4.

The guideway 6 comprises a convex bulge at the upper side of the lever arm 10 as well as an end region 11 extending straight and in parallel with the direction of the lever arm. The saddle point 12 is located between the convex bulge and the straight section.

The lever 5 is in its state of rest in the currentless starting state of the hose clamp in accordance with FIG. 1. If a hose is to be removed from the receiver 3 in this state or if a hose is to be placed into the receiver 3, the compression piece 1 can be raised by actuating the lever. In the starting position, the lever 5 is held in a horizontal position by the tension spring 8. The pin 7 of the compression piece 1 lies approximately at the center of the convex guideway 6. If the lever 5 is pivoted upwardly by a manual actuation starting from this position, the pin 7 lying on the guideway 6 and thus the compression piece 1 is raised against the mechanical spring force A. The maximum amplitude of this mechanical raising or opening of the clamp is achieved when the pin has arrived at the saddle point 12 of the lever 5 and a further raising is no longer possible due to the abrupt change in the gradient of the guideway 6.

The lever 5 is automatically pivoted back into its horizontal starting position after releasing the manual counterforce by the restoring force of the tension spring 8 directed in the direction D and by the restoring force of the compression piece 1 in direction A passed on to the lever 5 by the pin 7 via the guideway 6.

The lever 5 has no effect on the mechanical closing of the clamp in the currentless state, that is when it is actually not actuated.

FIG. 3 shows a sectional representation of a hose clamp in accordance with the invention in the currentless and manually opened state, as is shown in FIG. 2 for the hose clamp of the prior art.

Unlike the hose clamp of the prior art, a latch contour in the form of a recess 13 is arranged in the guideway 6 in accordance with the invention at the saddle point 12 of the lever 5. The recess 13 is of part circle shape in the embodiment shown, with the radius of the part circle corresponding to the outer radius of the pin 7.

If the pin 7 has run along the guideway 12 on a manual raising of the compression piece 1 for so long until the saddle point has been reached, the pin 7 drops into this recess. A return of the pin 7 along the guideway 6 is thereby prevented since the forces acting in the directions A and D press the pin 7 against the side surface of the recess 13, which results in a wedging or latching of the compression piece 1 with the lever 5. This prevents a pivoting back of the lever 5 into its horizontal position of rest and a lowering of the compression piece 1 in the direction A.

Different latching means such as a step at the guideway 6 are naturally also conceivable in addition to the shown molded shape 13.

In summary, the hose clamp therefore remains open in the currentless state after a mechanical opening of the clamp due to the latch contour.

This blockage caused by the latch contour 13 is released automatically and without further manual action on application of a current to the clamp. For on application of a current to the clamp, the compression piece 1 is additionally raised, starting from the position shown in FIG. 3 and the hose clamp is opened still a little further. The latch connection between the pin 7 and the latch contour 13 is released by magnetic raising going beyond the mechanical raising and the lever 5 is pivoted back (horizontally) into its starting position by the tension force of the spring 8 in the direction D. In operation, the function of the hose clamp in accordance with the invention is therefore identical to the function of the clamp of the prior art.

In summary, the inventive idea therefore comprises providing the hose clamp with a holding function, and in particular with a latching function, that can, for example, be manually activated in the evening so that the hose of the extracorporeal blood circuit is not clamped despite the currentlessness overnight. The latch function can be deactivated on the start of the device on the next day. In the course of the treatment, the clamp can then clamp the hose when the dialysis machine is currentless, as is known from the prior art.

The invention claimed is:

1. A hose clamp for a blood treatment device, said hose clamp comprising:
 a housing and an electromagnetically driven compression piece, with the electromagnetic drive of the compression piece being configured such that the compression piece is opened against a mechanical restoring force (A) in a state of the hose clamp with an applied current and is closed by the mechanical restoring force (A) in a currentless state of the hose clamp;
 a mechanical actuator with which the compression piece can be opened manually against the mechanical restoring force (A) in the currentless state of the hose clamp,
 with contact elements of the mechanical actuator and of the compression piece being configured such that the contact elements form a mechanical connection between the mechanical actuator and the compression piece after an opening of the compression piece in the currentless state, the connection preventing another closing of the compression piece in the currentless state of the hose clamp by the mechanical restoring force (A) and released with an applied current.

2. The hose clamp in accordance with claim 1, wherein a first of the contact elements is a projection and a second of the contact elements is a guideway, with the guideway being configured such that the projection moves along the guideway on actuation of the mechanical actuator, and with the guideway including a latch contour for the projection at a saddle point at which the projection is located in an opened position of the compression piece.

3. The hose clamp in accordance with claim 2, wherein the mechanical actuator is a pivotable lever.

4. The hose clamp according to claim 3, wherein the guideway is arranged at a side edge of a lever arm.

5. The hose clamp in accordance with claim 2, wherein the guideway is at least sectionally convex.

6. The hose clamp according to claim 5, wherein the guideway is partially of a circular shape.

7. The hose clamp in accordance with claim 2, wherein the projection is a pin.

8. The hose clamp according to claim 7, wherein the pin stands normal to the closing direction (A) of the compression piece.

9. The hose clamp in accordance with claim 2, wherein the latch contour is at least one of a recess in the guideway and a step on the guideway.

10. The hose clamp according to claim 2, wherein the first of the contact elements is at the compression piece side.

11. The hose clamp according to claim 2, wherein the second of the contact elements is at the actuator side.

12. The hose clamp in accordance with claim 1, further comprising a mechanical spring that is connected to the mechanical actuator and to the housing, and that exerts a restoring force (D) on the mechanical actuator against an actuation direction thereof on the opening of the compression piece.

13. The hose clamp according to claim 12, wherein the mechanical spring is a tension spring.

14. A blood treatment device comprising:
 an extracorporeal blood circuit having a line section configured as a hose,
 with a hose clamp in accordance with claim 1 being arranged at the line section configured as a hose.

15. The blood treatment device according to claim 14, wherein the blood treatment is device a dialysis device.

16. The blood treatment device according to claim 14, wherein the line section forms a part of an arterial line or of a venous line of the extracorporeal blood circuit.

17. A blood treatment device comprising: an extracorporeal blood circuit having a first line section and a second line section configured as hoses, with the first line section forming a part of an arterial line and the second line section forming a part of a venous line of the extracorporeal blood circuit:
 a first hose clamp and a second hose clamp, with the first hose clamp being arranged at the first line section and the second hose clamp being arranged at the second line section,
 with each of the first and second hose clamps having a housing and an electromagnetically driven compression piece, with the electromagnetic drive of the compression piece being configured such that the compression piece is opened against a mechanical restoring force (A) in a state of the first and second hose clamps with an applied current and is closed by the mechanical restoring force (A) in a currentless state of the first and second hose clamps,
 with the first and second hose clamps having a mechanical actuator with which the compression piece can be opened manually against the mechanical restoring force (A) in the currentless state of the first and second hose clamps, and
 with contact elements of the mechanical actuator and of the compression piece being configured such that the contact elements form a mechanical connection between the mechanical actuator and the compression piece after an opening of the compression piece in the currentless state, the connection preventing another closing of the compression piece in the currentless state of the first and second hose clamps by the mechanical restoring force (A) and released with an applied current.

18. A method of at least one of removing and inserting a hose kit from or into a blood treatment device hose kit forming at least a part of an extracorporeal blood circuit and including a line section configured as a hose at which a hose clamp is arranged, the hose clamp has having a housing and an electromagnetically driven compression piece, with the electromagnetic drive of the compression piece being configured such that the compression piece is opened against a mechanical restoring force (A) in a state of the hose clamp with an applied current and is closed by the mechanical restoring force (A) in a currentless state of the hose clamp, and a mechanical actuator with which the compression piece is openable manually against the mechanical restoring force in the currentless state of the hose clamp, and with contact elements of the mechanical actuator and of the compression piece being configured such that they form a mechanical connection between the mechanical actuator and the compression piece after an opening of the compression piece in the currentless state, the connection preventing another closing of the compression piece in the currentless state of the hose clamp by the mechanical restoring force (A) and released with an applied current, said method comprising steps of:

opening the compression piece the currentless state by actuating the mechanical actuator and at least one of removing and inserting the hose kit in the still currentless state of the hose clamp, while keeping the compression piece open by the mechanical connection between the mechanical actuator and the compression piece.

* * * * *